USOO5741228A

United States Patent [19]
Lambrecht et al.

[11] Patent Number: 5,741,228
[45] Date of Patent: Apr. 21, 1998

[54] IMPLANTABLE ACCESS DEVICE

[75] Inventors: Gregory H. Lambrecht, Mamaroneck; Joshua Makower, Nanuet, both of N.Y.; Sangeeta N. Bhatia, Cambridge, Mass.; David McDonald, Watertown, Mass.; Ashish Khera, Burlington, Mass.; J. Christopher Flaherty, Topsfield, Mass.; Alan K. Plyley; Russell J. Redmond, both of Goleta, Calif.; Claude A. Vidal, Santa Barabara, Calif.

[73] Assignee: Strato/Infusaid

[21] Appl. No.: 390,014

[22] Filed: Feb. 17, 1995

[51] Int. Cl.⁶ .................................................. A61M 11/00
[52] U.S. Cl. .......................... 604/93; 604/891.1; 604/256; 251/149.3
[58] Field of Search ................................ 604/256, 93, 167, 604/891.1, 175; 251/149.3

[56] References Cited

U.S. PATENT DOCUMENTS

| | | | |
|---|---|---|---|
| 4,645,495 | 2/1987 | Vaillancourt | 604/180 |
| 4,654,033 | 3/1987 | Lapeyre et al. | 604/175 |
| 5,053,013 | 10/1991 | Ensminger et al. | 604/167 |
| 5,057,084 | 10/1991 | Ensminger et al. | 604/167 |
| 5,180,365 | 1/1993 | Ensminger et al. | 604/93 |
| 5,195,980 | 3/1993 | Catlin | 604/167 |
| 5,226,879 | 7/1993 | Ensminger et al. | 604/93 |
| 5,263,930 | 11/1993 | Ensminger | 604/93 |
| 5,281,199 | 1/1994 | Ensminger et al. | 604/93 |
| 5,308,336 | 5/1994 | Hart et al. | 604/167 |
| 5,324,270 | 6/1994 | Kayan et al. | 604/167 |
| 5,350,360 | 9/1994 | Ensminger et al. | 604/93 |
| 5,352,204 | 10/1994 | Ensminger | 604/93 |
| 5,356,381 | 10/1994 | Ensminger et al. | 604/93 |
| 5,360,413 | 11/1994 | Leason et al. | 604/249 |
| 5,417,656 | 5/1995 | Ensminger et al. | 604/93 |
| 5,476,451 | 12/1995 | Ensminger et al. | 604/93 |

FOREIGN PATENT DOCUMENTS

| | | |
|---|---|---|
| 0110117 | 6/1984 | European Pat. Off. . |
| 0159260 | 10/1985 | European Pat. Off. . |
| WO8302063 | 6/1983 | WIPO . |
| WO9405246 | 3/1994 | WIPO . |
| WO9405351 | 3/1994 | WIPO . |

*Primary Examiner*—Mark Bockelman
*Attorney, Agent, or Firm*—Needle & Rosenberg, P.C

[57] ABSTRACT

An implantable access device for allowing repeat access to a site, space, device, or other object, fluid, tissue or region within the body of a patient. The implantable device, in one embodiment, includes a housing having an elongated open guidance channel that leads to an entrance orifice, a valve assembly communicating with the entrance orifice, and an exit orifice. The device permits access via the percutaneous insertion of an accessing filament such as a needle through the entrance orifice and into the valve assembly, which opens to allow the passage of fluids or other filaments such as guide wires or optical fibers. The device can be used for the introduction of therapeutic agents, for the infusion or withdrawal of fluids, or for the introduction of sensing, sampling, or treatment devices to another implanted device or to regions within the patient.

7 Claims, 6 Drawing Sheets

IMPLANTABLE ACCESS DEVICE

BACKGROUND OF THE INVENTION

The present invention pertains generally to an apparatus for providing access to a living body. More particularly, the invention relates to an improved implantable patient access device which allows for repeated access to a region within the body of a patient.

During a course of treatment, it may be necessary to gain repeat access to specific sites, devices, tissues, or fluids within the body of a patient. This may be effected for the temporary or sustained infusion of various therapeutic agents, the removal and treatment of fluids, the injection of contrast agents, as well as the insertion of various treatment devices such as fiber-optic cameras and light sources, ultrasound probes, and thrombectomy catheters. A number of strategies are currently used to gain such access, including direct vessel cannulation, short and long term catheterization, as well as subcutaneous port and pump implantation.

Direct cannulation of a native or artificial vessel with a needle provides perhaps the least expensive and simplest form of access. However, repeat cannulation of superficial vessels has been shown to result in vessel thrombosis, and in case of hemodialysis graft cannulation, access stenosis and the formation of pseudoaneurisms. A patient's accessible vessels can quickly be eliminated by repeat direct cannulation during the course of some aggressive treatment regimens, limiting treatment options and worsening prognosis. The use of large needles also leaves behind substantial lacerations in the vessel, requiring the application of pressure for a number of minutes to regain hemostasis, particularly in the case of high flow or high pressure vessels such as arteries, central veins, and primary or prosthetic fistulas. This pressure is uncomfortable for the patient and may result in early vessel thrombosis independent of other causes.

Short and long term catheters have been used to address the many problems of direct cannulation. These transcutaneous devices are generally flexible cannulae that are inserted percutaneously into the region of interest such as a blood vessel or the peritoneal cavity. Catheters have one or more lumens through which various fluids or devices can pass. While catheters allow repeat access with a reduced risk of vessel thrombosis, they suffer from a number of significant drawbacks. Aside from being unsightly and prone to inadvertent withdrawal, catheters often have complications with infection. The location of the infection is commonly the exit site or point at which the catheter passes through the skin. This essentially open wound provides a path for various hazardous organisms to migrate into the body and cause infections, either local or systemic. Infection has also been shown by a number of authors to increase the occurrence of both catheter and vessel thrombosis, other common complications of in-dwelling catheters.

Subcutaneously implanted ports have increasingly been used as an alternative to transcutaneous catheterization. These devices provide a site beneath the skin that can be accessed by special non-coring needles through a percutaneous puncture at the time of treatment. The devices generally comprise a housing that forms a reservoir which communicates with a catheter that leads to the area requiring treatment. A self-sealing septum formed from a high density silicone elastomer spans the top of this reservoir, creating a continuous barrier against the passage of fluids such as blood that are in communication with the port. This septum is punctured by the needle to permit access to the reservoir. Once the needle is withdrawn, the septum closes, restoring the continuous barrier. By being completely implanted (that is, requiring no open passage through the skin) ports avoid many of the infection complications of catheters. Ports are also generally better accepted by the patient because they are less obtrusive, cannot be accidentally withdrawn, and are easy to maintain.

Subcutaneously implanted ports are also used as a means of communicating with other implanted medical devices. For example, implantable infusion pumps that provide a sustained infusion of therapeutic agents into the body of a patient often use one or more integral ports as refilling and flushing sites. Various other devices, such as implanted inflatable prostheses, have exploited or may have benefited from the use of such ports as well.

Subcutaneously implanted ports do have a number of significant drawbacks that limit their application. First, their useful life is limited by the number of punctures that the septum can withstand before it leaks. Repeat access slowly degrades the silicone septum until ultimately it is unable to resist the passage of fluids or other elements that are in communication with the port. Secondly, they cannot be accessed by normal needles, requiring special, relatively expensive non-coring needles to reduce the damage done to the septum. This expense may seem minimal, but can be significant when aggressive therapies are required or when the therapies are primarily Medicare funded. Thirdly, only small needle gauges can be used even with non-coring needles because larger bore needles quickly destroy the septum. However, small needles are not appropriate for many treatments such as transfusion or hemodialysis which require high blood flows.

A series of prior art patents disclose an implantable patient access port which allows the introduction of various filaments including catheters and needles into the body of a patient without the use of a standard septum. By employing a variety of different valving mechanisms, the port presumably has broader applications to more rigorous therapies requiring frequent access or high flow, i.e. therapies previously restricted to transcutaneous catheters and direct cannulation. All of the ports illustrated and described in the patents incorporate a housing having a generally funnel-shaped entrance orifice, a valving mechanism that is opened by the accessing filament, allowing its passage, and an exit passageway.

One significant limitation of the foregoing prior concepts is in the strike area, or the region that the medical professional attempting access must hit with the accessing filament to enter the device. A large strike area is critical for simple cannulation and for allowing each insertion wound to heal before that region must be re-cannulated. By nature, to increase the strike area of a funnel such as that described in the art, one must also increase its overall size in three dimensions. A dimension of particular importance with ports is height, or depth from the skin inward. The taller a port, the more tension it places on the insertion wound, the more obvious its presence to observers, and potentially the greater chance for erosion and infection. So increasing the strike area of the funnel, increases the size of the port in three dimensions, potentially leading to complications.

The funnel-shaped entrance orifice further limits the strike area by providing only a single focal point or entry point for the accessing filament. Because the filament is always focused to the same site, the same tissue proximal to that entry site must be traumatized during each access. Repeat trauma to tissue can lead to devascularization and necrosis, creating a potential site for infection.

Another limitation of prior art concepts is the durability of the valve assembly when sharp needles or trocars are used for access. While there exist various concepts that allow access by either flexible filaments such as catheters or rigid filaments like needles, all of the valve assemblies allowing access specifically by rigid filaments are either subject to direct contact with the sharp tip of the accessing needle promoting wear or do not specifically seal around the accessing filament before the valve assembly is open or before it closes. In certain known devices, elastomeric members which form the valve assembly are in the direct path of the accessing needle. The hole in the first elastomeric member is smaller in diameter than the accessing filament, and hence will suffer damage every time the accessing needle is inserted. This damage could ultimately lead to valve failure, which can have catastrophic consequences for the patient.

In certain prior art designs, movement of the valve components is directly linked with movement of the sealing components so that creation of a seal around the accessing filament requires the valve to be opened. The leaflets of the valve are either in direct sealing engagement with the filament sealing element or the motions of the two elements are directly linked through an intervening rigid member. These designs imply that some throw or partial opening of the valve is required before the seal is created around the accessing filament or, more importantly, that flow is potentially allowed through this partially open valve and around the accessing filament until the valve has been opened far enough to generate an effective seal. This could potentially lead to the repeat formation of hematomas or passage of other fluids into the tissue surrounding the device as a result of access.

The primary objective of the present invention is to provide an implantable patient access device which overcomes many of the deficiencies of prior art ports. Specifically, in one embodiment, the implantable access device that forms this invention employs an open guidance channel that allows for increases in accessing filament strike area without increasing the overall height of the device. Further, the device employs a valve assembly that provides access to the patient while at all times maintaining a fluid tight seal around the accessing filament, normally a needle. The valve assembly does not allow contact of the accessing filament's sharp leading edges, particularly in the case of a needle, with any soft elastomeric member of the valve assembly. In this way, the valve assembly allows repeat access by standard needles of either small or large gauge, eliminating many of the access problems that have limited the use of standard ports with septums and some other prior art devices. Further, the valve assembly ensures that a seal around the accessing filament will be formed prior to the valve assembly opening to allow access to the patient. This is accomplished in one embodiment of the invention by ensuring that less movement of the accessing filament is required to create a seal about the filament than is required to begin opening the valve, and in another embodiment of the invention by completely decoupling creation of the seal from motion of the valve. The assembly thus ensures that there is no leakage of fluids around the accessing filament at any time during access. Other advantages of the present invention are described below.

SUMMARY OF THE INVENTION

The present invention is directed toward an implantable patient access device comprising a housing having at least one entry port and at least one exit port with a passageway extending therebetween, with the housing further comprising an elongated open guidance channel disposed therein communicating with the entry port, with the channel having a substantially constant cross sectional area and with the channel further being adaptable to receive a filament for guiding the filament toward and into the entry port, and with the housing further including a valve assembly disposed in the passageway, the valve assembly adapted to be activated by the filament after passage of the filament through the entry port, the valve assembly being normally closed but adapted to be opened by the filament to allow access to the patient or to a site, space, device, or other object, tissue, or fluid within the patient by the filament. The valve assembly comprises a sealing element and a valve disposed in the passageway, with the sealing element first creating a seal about the filament before the valve assembly opens to allow access to the patient by the filament. The sealing element maintains the seal about the filament until after the valve assembly closes. The channel might have a generally V-shaped cross section or it might have a generally U-shaped cross section such as a parabola. The valve might comprise a miter valve or a slit valve, with each valve adapted to be opened by movement of the filament into the valve assembly. Alternatively, the valve might comprise in combination a plug seated in sealing engagement within the passageway and a slit valve, the plug and the slit valve being forced from sealing engagement with the passageway by movement of the filament through the passageway. Additionally, the valve might comprise a plug seated in sealing engagement within the passageway and an opening proximate to the plug such that when the plug is forced from sealing engagement with the passageway by movement of the filament through the passageway the opening allows access to the patient or site, space, device, or other object, tissue, or fluid within the patient by the filament. The sealing element comprises an elastomeric member with a first and second end and an open conduit therebetween, with the first end being substantially fixed in position within the housing and with the second end having a resilient cap affixed thereto, the cap being adapted to withstand repeat contact with the filament, resisting passage of the filament such that when the filament is advanced through the conduit the filament makes contact with the cap causing the elastomeric member to stretch and collapse around the filament. The elastomeric member has an outer dimension, the outer dimension at a first location having a first magnitude which decreases to an outer dimension of a second magnitude at a second location, the decrease corresponding to a decrease in dimension of the passageway such that when the elastomeric member is stretched by advancement of the filament, the larger outer dimension of the elastomeric member is compressed against the accessing filament within the smaller dimension of the passageway. The housing further comprises means for retaining an accessing filament in a fixed position within the housing. The exit port is adapted to be connected to a catheter, a graft or an implanted medical device.

The invention further embodies an implantable patient access device comprising a housing having at least one entry port and at least one exit port with a passageway extending therebetween, the entry port being adapted to receive a filament for passage into the passageway, the housing further including and disposed in the passageway a valve assembly comprising a valve and a sealing element, the valve assembly adapted to be activated by the filament after passage of the filament through the entry port whereupon a seal, independent of activation of the valve, is created by the sealing element about the filament before the valve opens to allow access to the patient or site, space, device, or other object, tissue, or fluid within the patient by the filament. The valve might comprise a miter valve or a slit valve, with each valve adapted to be opened by movement of the filament into the valve assembly. The valve might comprise an elastomeric plug seated in sealing engagement within the passageway, the plug being forced from sealing engagement with the passageway by movement of the filament through the passageway. The sealing element comprises an elastomeric member with a first and second end and an open conduit therebetween, the first end being substantially fixed in position within the housing and the second end having a resilient cap affixed thereto, the cap being adapted to withstand repeat contact with the filament, resisting passage of the filament such that when the filament is advanced through the conduit the filament makes contact with the cap causing the elastomeric member to stretch and collapse around the filament. The elastomeric member has an outer dimension, the outer dimension at a first location having a first magnitude which decreases to an outer dimension of a second magnitude at a second location, the decrease corresponding to a decrease in dimension of the passageway such that when the elastomeric member is stretched by advancement of the filament, the larger outer dimension of the elastomeric member is compressed against the accessing filament within the smaller dimension of the passageway creating a seal about the filament. The housing might further comprise means for retaining an accessing filament in a fixed position within the housing. The filament might be a needle having a point and the housing might further include means for guiding the needle through the conduit and into the resilient cap such that the point of the needle contacts only the resilient cap. The exit ports in these devices are adapted to be connected to a catheter, a graft or an implanted medical device.

The invention additionally embodies an implantable patient access device comprising a housing having a plurality of entry ports and a plurality of exit ports with a passageway extending between each entry port and each exit port, with the housing further comprising a plurality of elongated open guidance channels disposed therein, each of the guidance channels communicating with an entry port, each of the guidance channels having a substantially constant cross sectional area, with each of the guidance channels further being adaptable to receive a filament for guiding the filament toward and into an associated entry port, the housing further including a valve assembly disposed in each passageway, the valve assembly adapted to be activated by the filament after passage of the filament through the entry port, the valve assembly being normally closed but adapted to be opened by the filament to allow access to the patient or site, space, device, or other object, tissue, or fluid within the patient by the filament.

DETAILED DESCRIPTION OF THE PREFERRED EMBODIMENTS

Figure 1:
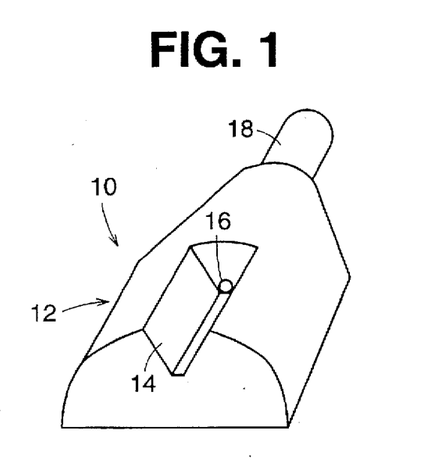
FIG. 1 is a schematic perspective view of a first embodiment of an implantable patient access device in accordance with the principles of the present invention and illustrating an elongated open generally V-shaped entrance guidance channel.

The description herein presented refers to the accompanying drawings in which like reference numerals refer to like parts throughout the several views. Referring to FIG. 1, in accordance with the principles of the present invention, there is illustrated a schematic perspective view of a first embodiment of an implantable patient access device 10. The excess device 10 includes a housing 12 having defined therein an elongated open guidance channel 14 communicating with entry port 16 of the housing. In this figure the guidance channel is shown to be of a generally V-shaped configuration but other configurations would be possible. Port 16 in turn is in fluid communication with housing exit port 18. The internal structure of device 10 will be shown in greater detail in subsequent views.

Figure 2:
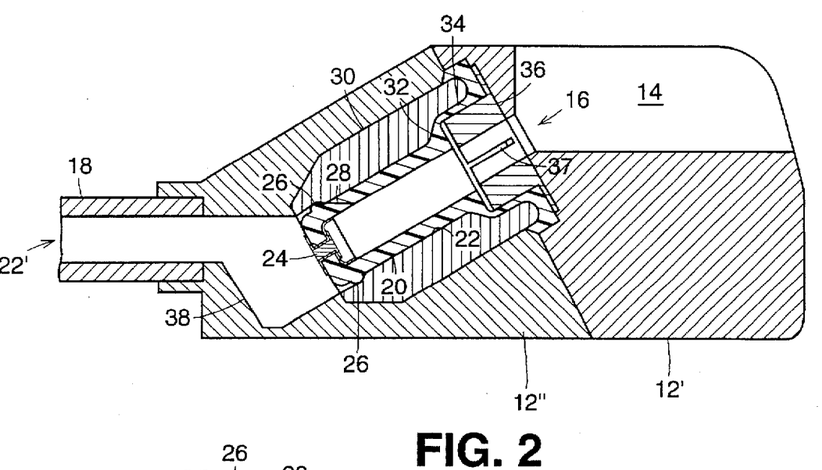
FIG. 2 is an enlarged longitudinal sectional view of the device depicted in FIG. 1.
Figure 2A:
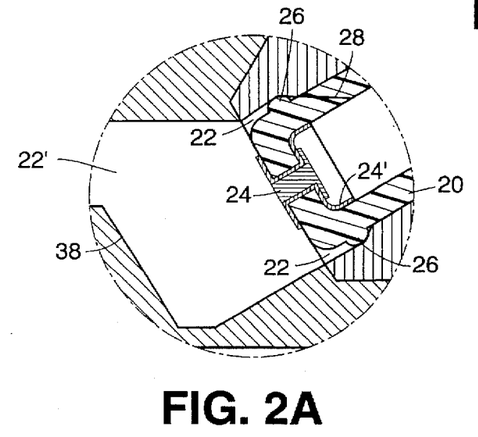
FIG. 2A is a further enlarged view of a portion of the device illustrated in FIG. 2 showing a partial view of the valve assembly of the device.

Turning now to FIG. 2, there is depicted an enlarged longitudinal sectional view of implantable patient access device 10 depicted in FIG. 1. Here there is shown an elastomeric member 20 disposed in passageway 22 of device 10. Elastomeric member 20, in this embodiment, includes a plug 26, a slit valve 28 and terminates in a cap 24. Cap 24 may be titanium, stainless steel or any other suitable resilient metal. Elastomeric member 20 is positioned within a housing insert 30. Housing insert 30 is employed for ease of manufacture, but it should be understood that it could also be integral in the geometry of housing 12. Here housing 12, for ease of manufacture, is shown to be composed of part 12' and part 12". Elastomeric member 20 further has a transition region 32 along which the outer diameter of the elastomeric member 20 decreases from a first larger diameter to a second smaller diameter. The interaction between the elastomeric member 20, specifically its transition region 32, and the housing insert 30 will create a seal around an accessing filament as will be further described below. Elastomeric member 20 has a substantially thinner walled section 34 above transition region 32. Also within passageway 22 is a filament retention piece 36. Exit port 18 extends from housing part 12" and forms lumen 22' which is in fluid communication with passageway 22. Exit port 18 is adaptable to be coupled to a catheter, graft, another device or conduit that is within and/or in communication with the body of a patient. Also shown here as part of housing part 12", is a limiter 38 which stops the downward movement of the activated valve assembly. FIG. 2A is an enlarged view of the left portion of FIG. 2. FIG. 2A shows the plug 26 at the distal end of the elastomeric member 20 in a sealing engagement with passageway 22, and slit valve 28 in a closed position. FIG. 2A also depicts cap 24 and filament landing 24'.

Figure 3:
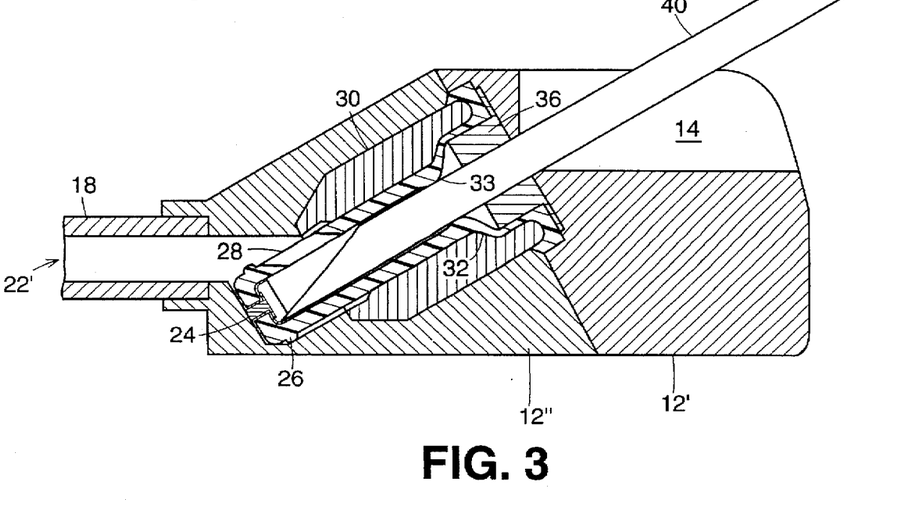
FIG. 3 is a view much like that of FIG. 2 but further showing the valve assembly of the device being activated by an accessing filament.
Figure 3A:
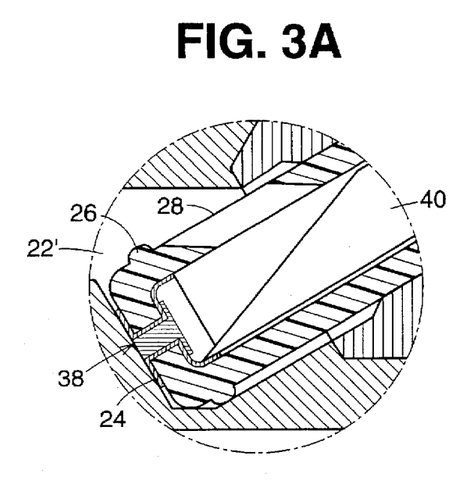
FIG. 3A is an enlarged view much like that depicted in FIG. 2A but further showing the valve assembly after activation by the accessing filament.
Figure 3B:
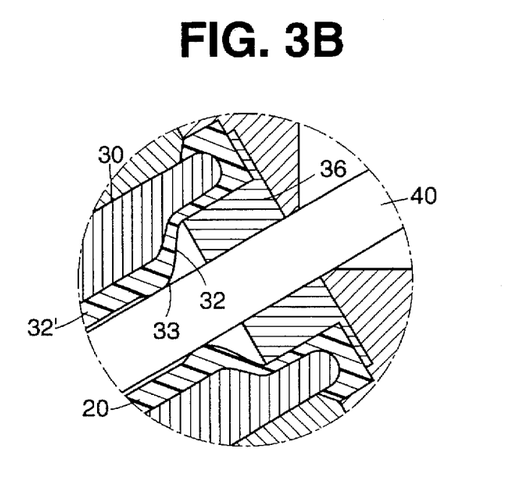
FIG. 3B is an enlarged view of another portion of the device illustrated in FIG. 3 showing a seal created about the accessing filament.
Figure 4:
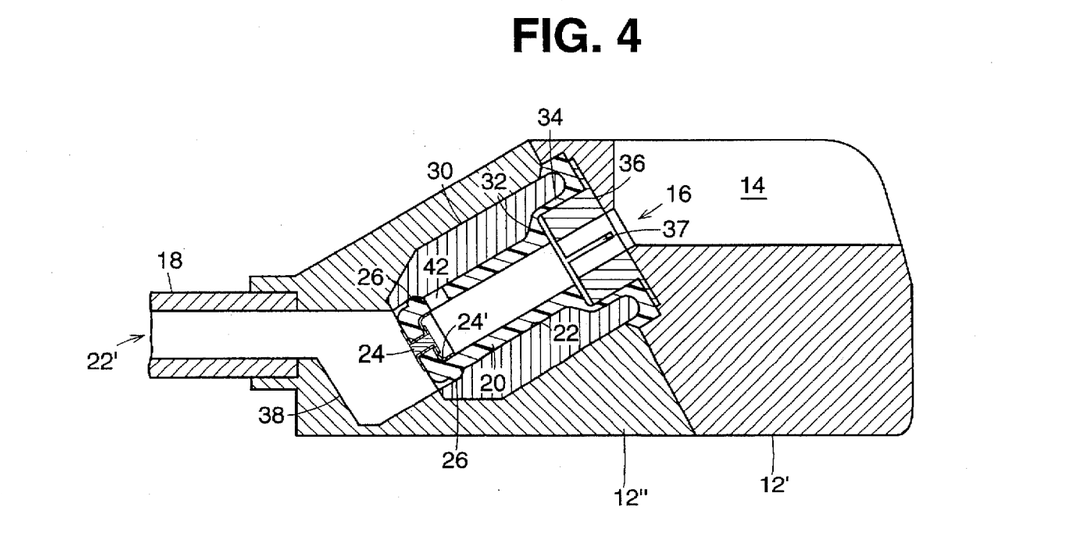
FIG. 4 is a view substantially like that of FIG. 2 but depicting an alternate embodiment of the valve of the invention.
Figure 5:
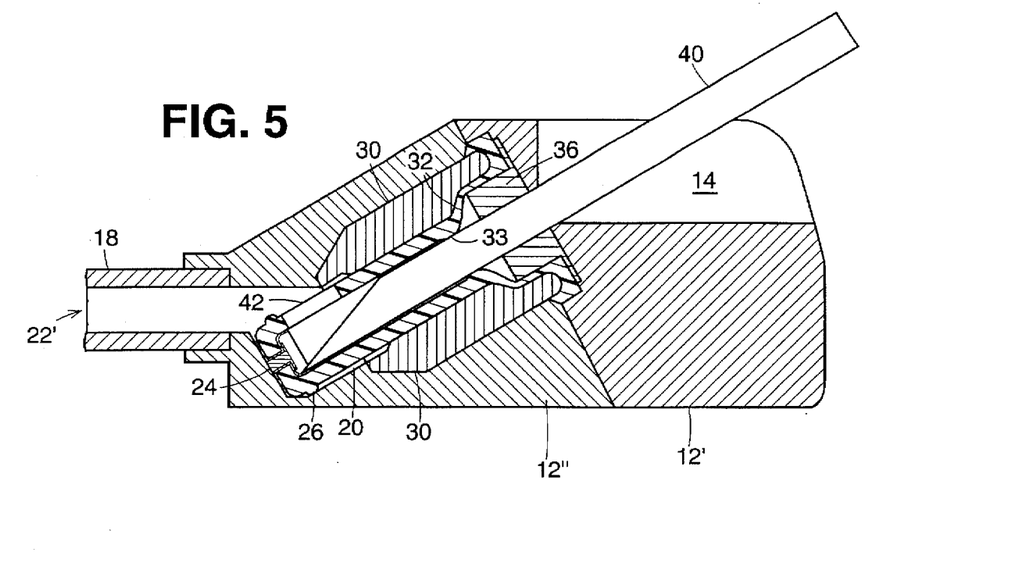
FIG. 5 is a view substantially like that of FIG. 3 but depicting the valve arrangement of FIG. 4.

Turning now to FIG. 3, there is shown the patient access device of FIG. 2 with an accessing filament 40 opening the plug 26 and the slit valve 28. Preferably the filament is substantially rigid. Typically the filament would be a needle but a catheter or other substantially rigid member could be used. Before movement of plug 26 out of passageway 22 and the opening of slit valve 28 which would allow communication between filament 40 and lumen 22', a seal 33 is first created about filament 40. Seal 33 is maintained at all times when plug 26 and slit valve 28 allow communication between the filament 40 and lumen 22' and the seal is released only after plug 26 returns to a sealing engagement within passageway 22. FIG. 3A shows an enlarged view of the valve comprising plug 26 and slit valve 28 in an open position. FIG. 3B is an enlarged view which shows in greater detail the seal 33 about accessing filament 40. Seal 33 is generated when the transition region 32 of elastomeric member 20 is pulled into the smaller diameter 32' of housing insert element 30, compressing the elastomeric member 20 against the accessing filament 40. Further in FIG. 3B is shown the filament retention piece 36 engaging accessing filament 40. The filament retention piece 36 is configured with an inner dimension smaller than the outer dimension of the accessing filament 40, such that as the accessing filament 40 is introduced into entry port 16, the filament retention piece 36 expands and applies a force against the accessing filament 40 to resist its withdrawal from entry port 16. Filament retention piece 36 may employ a strain release slot or slots 37 to tune the force applied to accessing filament 40 and increase its useful life span. FIGS. 4 and 5 are substantially the same as FIGS. 2 and 3, the primary difference being that slit valve 28 has been replaced by an opening 42 located in elastomeric member 20.

Figure 6:
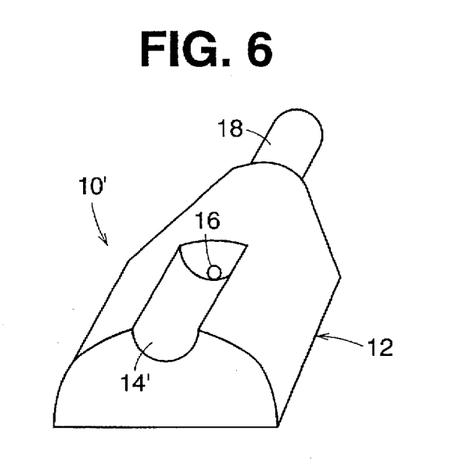
FIG. 6 is a view much like that of FIG. 1 but showing an elongated open generally U-shaped entrance guidance channel.

FIG. 6 is substantially the same view as that shown in FIG. 1 except that here the device has been designated 10' and the guidance channel 14' has a generally parabolic or generally U-shaped cross section. A guidance channel having a flat rather than a curved bottom is also considered to be of a generally U-shaped configuration. The generally U-shaped configuration is but one of the many possible configurations suitable for the elongated open guidance channel of the invention.

Figure 7:
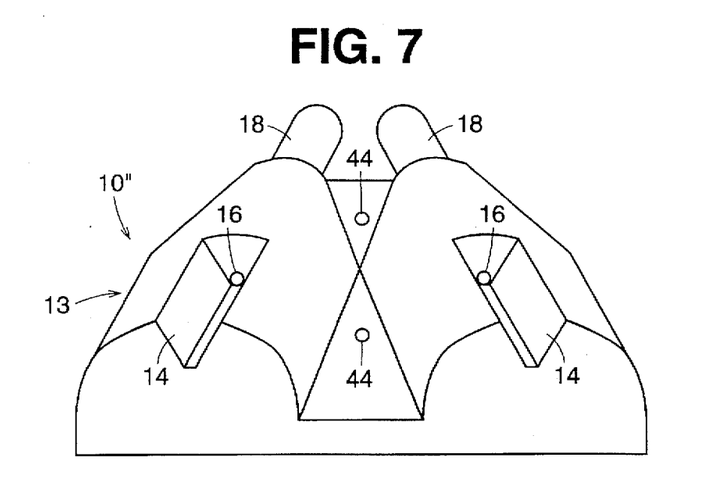
FIG. 7 is a view similar to FIG. 1 but illustrating a device having multiple entrance guidance channels and exit ports.

FIG. 7 depicts a dual patient access device 10" configuration with two complete devices (each having any of the valve assemblies described herein) fixedly coupled in a housing 13 to simplify the implantation of two devices. FIG. 7 also shows two suture holes 44 for anchoring the device to the patient. Suture holes 44 are only one of the many possible anchoring means for these devices. While not shown, any of the devices that form this invention can employ an anchoring means such as suture holes 44.

Figure 8:
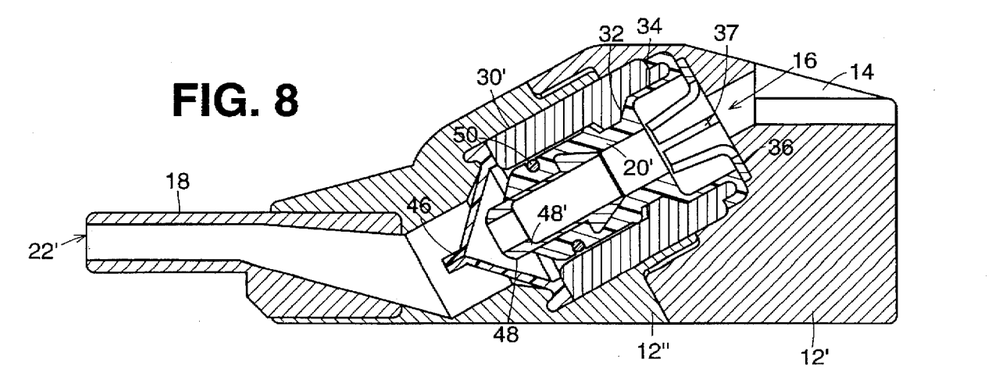
FIG. 8 is a view much like that of FIGS. 2 and 4 but depicting an alternate embodiment of a valve assembly with the valve assembly closed.
Figure 9:
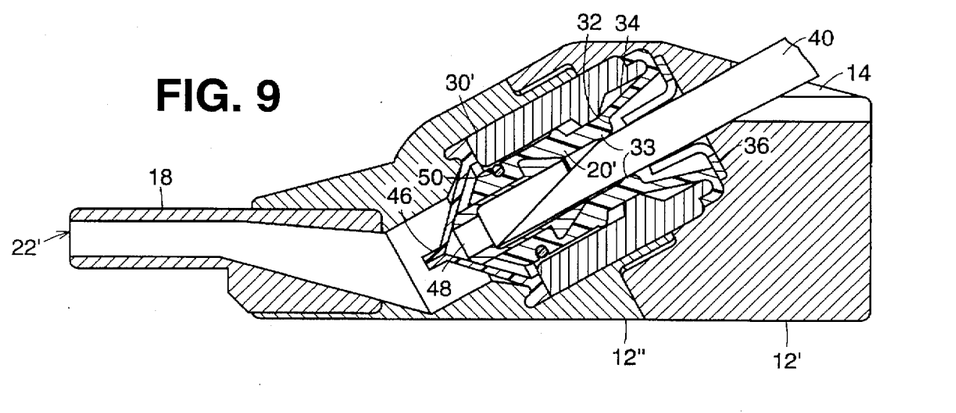
FIG. 9 is a view much like that of FIG. 8 but depicting a seal created about the accessing filament but with the valve closed.
Figure 10:
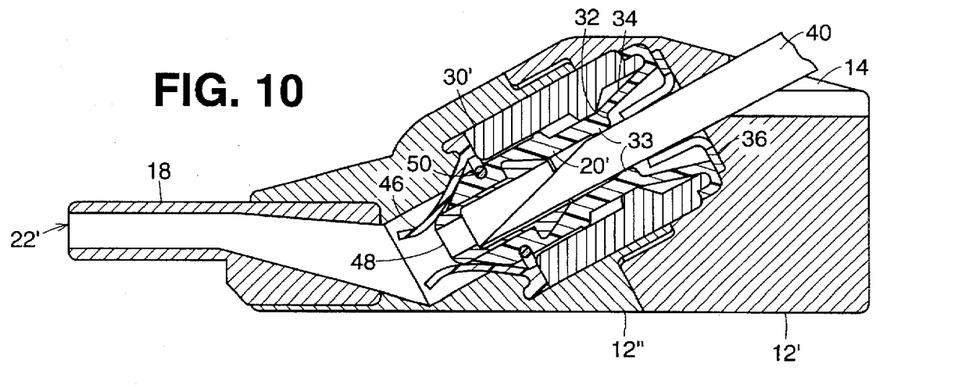
FIG. 10 is a view much like that of FIG. 9 with the seal maintained but the valve open.

FIGS. 8 through 10 depict another embodiment of the present invention which employs a duck bill or miter valve 46 in place of plug 26 and slit valve 28 or opening 42. Cap 48, having a filament landing or strike area 48', has replaced cap 24. A fastener 50 assists in maintaining the coupling between elastomeric member 20' and cap 48. Elastomeric member 20' has all of the attributes of elastomeric member 20. FIG. 8 depicts the valve assembly prior to activation. Also shown in FIG. 8, is housing insert 30' which is substantially like housing insert 30. The remaining structural elements are like those herein described in respect to the other embodiments of the invention. FIG. 9 additionally depicts an accessing filament 40 which moves cap 48 and elastomeric element 20' to create a seal 33 about filament 40 before valve 46 is opened. FIG. 10 shows further advancement of filament 40 and cap 48 which opens valve 46 to provide access to a patient or a site, space, device, or other object, tissue, or fluid within the patient. As shown here and as is shown in all other embodiments of the invention, seal 33 is created about the accessing member before the respective valve is opened, the seal is maintained during the time that the valve is open and the seal is not released until after the valve is closed.

Figure 11:
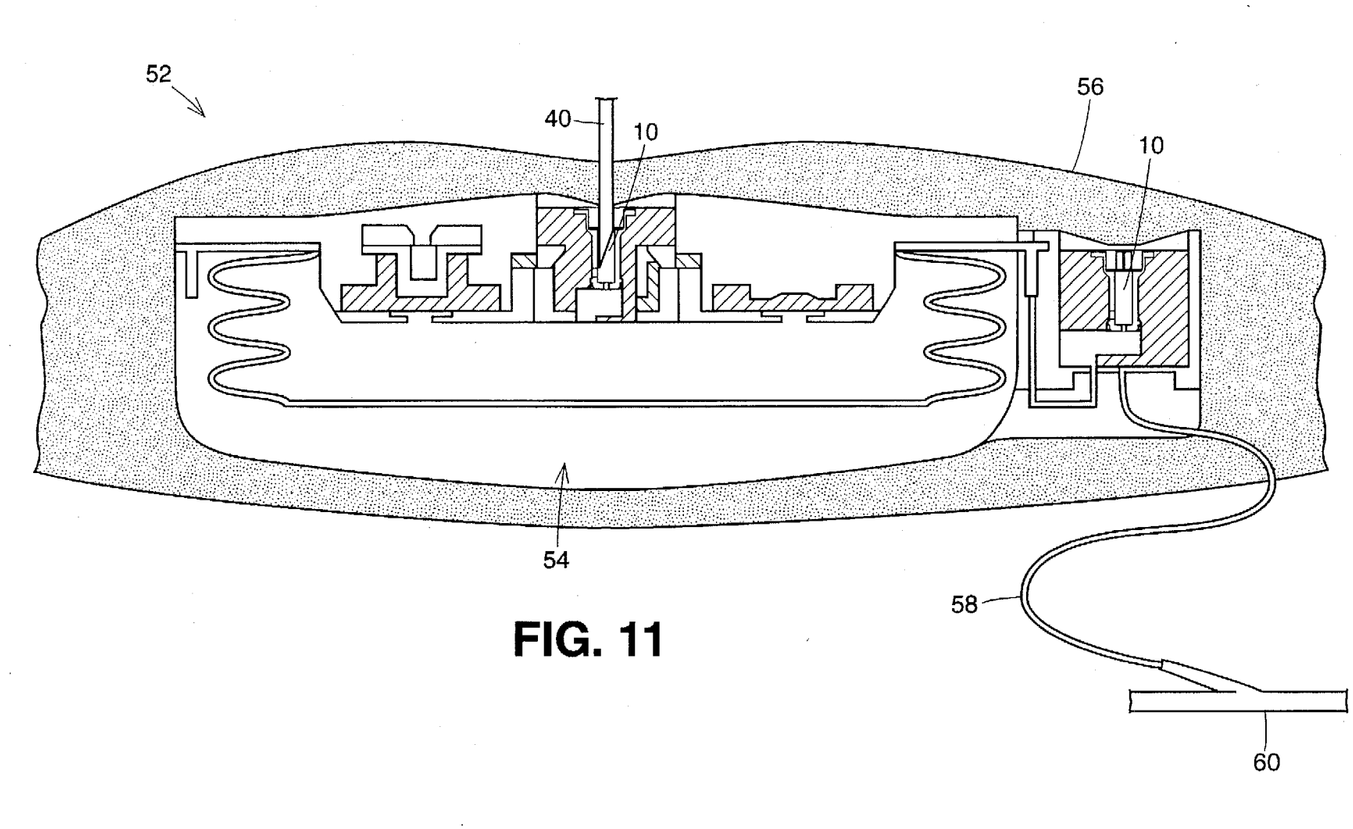
FIG. 11 schematically depicts an embodiment of the present inventive device as an integral part of an implanted medical apparatus.

Turning lastly to FIG. 11, there is shown a schematic view of device 10 of the present invention as an integral functioning part of an implantable medical apparatus 52, such as a sustained infusion pump 54. Here two devices are shown. However, it should be understood that one or a number of devices could be employed, such as 10, 10', 10". In this view, pump 54 has been implanted below skin line 56 of a patient. Additionally shown is catheter 58 fluidly coupled to lumen 22' (not depicted in this view). The catheter is in fluid communication with a vessel 60, however, communication could be with a site, space, tissue, fluid, organ or another implanted device. Although not shown in this view, it also should also be understood that, like in FIG. 11, each of the devices of FIGS. 1–10 are adaptable for inclusion as an integral part of an implanted medical apparatus or adaptable for independent implantation under the skin of a patient for communication with a site, space, tissue, fluid, vessel, organ, or the like.

An important characteristic of the various valve assemblies is the timing of the valve opening and closing relative to the seal formed around the accessing filament. Each valve assembly forms a seal around the accessing filament before the valve opens allowing access to the patient, and then releases that seal only after the valve has again been closed. This prevents any possibility of hemorrhage or reflux of fluids or gases out the device.

The open guidance channels that are part of this invention have a number of advantages over the funnels described in the prior art. First, they allow for increases in strike area without an increase in overall device height. With a device of the configuration shown in FIG. 1, the strike area is increased simply by increasing the length of the device. Another advantage of the channel is that it allows the device to better simulate a natural vessel both in shape and the way in which it is accessed. This may make the device and its use more readily apparent to the accessing nurse or physician. Finally, an elongated open channel could allow for multiple entry sites along the channel's length, unlike a funnel which is limited to a single focal point. By accessing different entrance orifices during a treatment that requires repeat access procedures, trauma to the same tissue can be minimized relative to the funnel with its single focal orifice.

The device in FIG. 3 consists of a three-part housing, a needle retention piece, and a wedge seal and plug valve assembly. A first piece 12' of the housing could be made of a resilient material such as titanium that could endure frequent contact with the sharp tip of an accessing filament such as a needle. The guide channel that is an integral part of piece 12' is one of the many possible open channel forms described by this invention. The channel depicted in FIG. 3 could be employed as a filament guide. The base of this guide channel could be sloped from a first end towards the entrance orifice at an angle suitable for allowing the accessing filament to slide easily upon contact as well as for decreasing the overall volume of the device. The walls of this channel may be, to name but a few configurations, vertical, sloped or rounded. Extending laterally from either side of piece 12' at its base could be two suture loop attachment sites for facilitating fixation of the device within the body. Any suitable number of attachment points can be used. FIG. 7 illustrates but one potential fixation configuration. Alternatively, the exterior surface of the housing can be roughened or porous, promoting tissue ingrowth to help fix the device within the patient.

A second piece 12" of the housing can be made either of a resilient material or of a more easily molded material such as plastic. This piece forms much of the flow path for the fluids that could be infused or removed through the complete device. To decrease the necessary flush volume and the risk of fluid pooling, the diameter of the flow path is closely matched to the diameter of the accessing filament. A third piece 18 is a simple tube insert that provides a surface along which a catheter or graft may be joined with the patient access device. Again, this piece could be constructed from either a resilient or moldable plastic material. The exit port may provide communication with an implantable medical device and may be of another configuration more suitable to optimizing its function in a certain application. Filament retention piece 36 is a simple tube with a flanged end. It should be constructed of a resilient material capable of withstanding frequent contact with a sharp accessing filament. The tube is slotted along all or part of its axial length and is of a diameter to some degree less than the diameter of the accessing filament. Hence when the accessing filament such as a needle is inserted, the tube expands elastically, applying a force normal to the filament about its circumference. This force creates a friction that is sufficient to retain the filament in an engaged position during the access procedure.

The wedge seal and plug valve assembly consists of three functional parts. The first is a tube-like structure (20) formed from an elastomer such as silicone rubber. The second is a small cap (24) formed of a resilient material which is fixed to the distal end of the tube, but can be fixed to the tube at any appropriate site. The third piece is a simple insert (30) that is either a separate piece as depicted or is part of the geometry of the second piece of the housing. The tube is clamped into place at its proximal end just beyond the entrance orifice and filament retention piece. The tube fits within the internal structure of the insert. The outer diameter of the tube mirrors the interior shape of the insert along most of its length, being greatest at the most proximal end, narrowing along a short transitional length, and then remaining constant up to a point near the distal end. It should be understood that the term proximal, when referring to FIG. 2 for example, is that location towards the right of the figure while the term distal refers to that location towards the left of the figure. At the distal location of the tube, an annular plug (26) bulges radially from the tube to a diameter greater than the corresponding interior diameter of the insert. This plug acts as the valve, sealing against fluids or gases when the tube is recessed within the insert and the plug is compressed against the insert's interior. Just above this plug is either a hole or slit through the wall of the tube which becomes a passageway for fluids or filaments when the valve is open. The tube has an internal diameter that is larger than that of the specified accessing filament. The proximal portion has the largest internal diameter to allow the filament retention piece to fit recessed within the tube. This portion of the tube also has the thinnest wall, making it the most flexible section. When an accessing filament is inserted into the device it makes contact only with the retention piece and the cap at the tube's distal end. Further advancement of the filament causes the elastomeric tube to stretch, particularly in the thinner proximal section. This stretch pulls the thicker transitional length of tube into the narrower portion of the insert, compressing the tube between the wall of the insert and the circumference of the filament. This compression creates a seal. When the annular plug at the distal portion of the tube is pushed beyond the distal portion of the insert, the opening above this plug is exposed to the exit port allowing fluids to be infused and withdrawn or instruments to be inserted into the body of the patient.

The valve only opens once the seal has been created about the accessing filament and closes before that seal is broken. This is ensured by the travel necessary to push the annular plug out of sealing engagement with the interior wall of the insert. This travel is specified to be longer than the travel necessary to generate a seal around the accessing filament.

The device depicted in FIGS. 8–10 uses a miter or duck bill valve (46) as the valving element. Typically the miter valve comprises elastomeric elements or components. The valve is opened as the cap at the distal end of the elastomeric tube is pushed into the valve by the advancing filament or needle. This cap would again be formed from a resilient material such as stainless steel, titanium or other suitable metal. The cap has a simple step decrease in internal diameter from the proximal portion to the distal portion. The larger diameter allows passage of certain specified filaments or needle gauges, while the smaller diameter acts to limit passage of those filaments or needles, but allows for fluid flow.

The duck bill valve may have some advantages over the side hole valve of FIG. 4 or the slit valve of FIG. 2. It provides a more direct and potentially smoother fluid flow and instrument insertion pathway. This may ease insertion of various devices and allow for higher infusion flow rates at lower pressures. Another distinct advantage of this valve assembly is that creation of the seal about the accessing filament requires no motion of the valve. By decoupling the sealing element from the valve and by separating the two elements, the design ensures that the seal will be created about the filament before the valve opening is initiated.

The use of a channel in these devices allows the overall device to better simulate a natural artery or vein. By running down the central axis of the device, a channel, as herein described, would allow the accessing medical professional to access the port in much the same way they access peripheral vessels, i.e. by placing fingers on either side of the vessel and sticking for its center. The length of this channel can be chosen to fit the requirements of the specific therapy, allowing for an increase in overall strike area by increasing the size of the implantable access device in only a single dimension.

We claim:

1. An implantable access device comprising a housing having at least one entry port and at least one exit port with a passageway extending therebetween, said housing further comprising an elongated open entrance guidance channel disposed therein having a tenth and communicating with said entry port, said channel having a substantially constant transverse cross sectional area substantially along the length, with substantially constant cross sectional area substantially along the length, with said channel further being adaptable to receive a filament for guiding said filament toward and into said entry port, and with said housing further including a valve assembly disposed and into said entry port, and with said housing further including a valve assembly disposed in said passageway, said valve assembly adapted to be activated by said filament after passage of said filament through said entry port, said valve assembly being normally closed but adapted to be opened by said filament to allow access through said exit port, wherein said valve assembly comprises a sealing element and a valve disposed in said passageway, with said sealing element being positioned closer to said entry port than is said valve, said filament and said sealing element coacting to first create a seal about said filament before said valve opens to allow said access, and wherein said sealing element comprises an elastomeric member with a first end and a second end and an open conduit therebetween, said first end being substantially fixed in position within said housing and said second end having a resilient cap affixed thereto, said cap being adapted to withstand repeat contact with said filament, resisting passage of said filament such that when said filament is advanced through said conduit the filament makes contact with said cap causing said elastomeric member to stretch and collapse around said filament.

2. The device according to claim 1 wherein said elastomeric member has an outer dimension, said outer dimension at a first location having a first size which decreases to an outer dimension of a second size at a second location, said decrease corresponding to a decrease in dimension of said passageway such that when said elastomeric member is stretched by advancement of said filament, the larger outer dimension of said elastomeric member is compressed against said accessing filament within the smaller dimension of said passageway.

3. An implantable access device comprising a housing having at least one entry port and at least one exit port with a passageway extending therebetween, said entry port being adapted to receive a filament for passage into said passageway, said housing further including and disposed in said passageway a valve assembly comprising a valve and a sealing element, said sealing element comprising an elastomeric member with a first and second end and an open conduit therebetween, said first end being substantially fixed in position within said housing and said second end having a resilient cap affixed thereto, said cap being adapted to withstand repeat contact with said filament, resisting passage of said filament such that when said filament is advanced through said conduit the filament makes contact with said cap causing said elastomeric member to stretch and collapse around said filament, said valve assembly adapted to be activated by said filament after passage of said filament through said entry port whereupon a seal, independent of activation of said valve, is created by said sealing element about said filament before said valve opens to allow access through said exit port.

4. The device according to claim 3 wherein said valve comprises a miter valve.

5. The device according to claim 3 wherein said housing further comprises means for retaining an accessing filament in a fixed position within said housing.

6. The device according to claim 3 wherein said exit port is adapted to be connected to a catheter, a graft, or an implanted medical device.

7. The device according to claim 3 wherein said filament is a needle having a point and wherein said housing further includes means for guiding said needle through said conduit and into said resilient cap such that said point of said needle contacts only said resilient cap.

* * * * *

UNITED STATES PATENT AND TRADEMARK OFFICE
Certificate

Patent No. 5,741,228                                                       Patented: April 21, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gregory H. Lambrecht, Mamroneck, NY; Joshua Makower, Nanuet, NY; Sangeeta N. Bhatia, Cambridge, MA; David McDonald, Watertown, MA; Ashish Khere, Burlington, MA; J. Christopher Flaherty, Topsfield, MA; Alan K. Plyley, Goleta, CA; Russell J. Redmond, Goleta, CA; Claude A. Vidal, Santa Barbara, CA; and Brett Stern, New York, NY.

Signed and Sealed this Fourteenth Day of August, 2001.

ANGELA D. SYKES
*SPE*
Art Unit 3762